United States Patent

Paap et al.

[11] 4,228,350
[45] Oct. 14, 1980

[54] METHOD AND APPARATUS FOR MEASURING UNDERGROUND FLUID FLOW CHARACTERISTICS

[75] Inventors: Hans J. Paap; Albert P. Richter, Jr.; Harold E. Peelman; Dan M. Arnold; Hubert D. Scott, all of Houston, Tex.

[73] Assignee: Texaco Inc., White Plains, N.Y.

[21] Appl. No.: 859,357

[22] Filed: Dec. 12, 1977

[51] Int. Cl.$^2$ ............................................. G01V 5/00
[52] U.S. Cl. ...................... 250/267; 250/270
[58] Field of Search .............. 250/269, 270, 261, 262, 250/267

[56] References Cited

U.S. PATENT DOCUMENTS

| 3,180,409 | 4/1965 | Dewan | 250/269 |
| 3,862,418 | 1/1975 | Preiss | 250/269 |
| 4,051,368 | 9/1977 | Arnold et al. | 250/270 |

Primary Examiner—Alfred E. Smith
Assistant Examiner—Janice A. Howell
Attorney, Agent, or Firm—Carl G. Ries; Thomas H. Whaley; William J. Beard

[57] ABSTRACT

An underground logging tool is equipped with a gamma ray detector encircled by a rotatable shield featuring a collimator slot. After the fluid in a formation is activated by a neutron source, the detector is used to obtain radiation count information as a function of horizontal direction as the shield is rotated. Comparison of count rate data as a function of the shield slot orientation gives information concerning the direction of the formation fluid flow. Measurements at different time intervals following the activation of the fluid, made with the shield retracted from the detector, may also be interpreted in terms of speed of horizontal fluid flow past the tool.

23 Claims, 14 Drawing Figures

*ACTIVATION AND DECAY IN VOLUME ELEMENT*

*FIG. 11*

*NOMOGRAPH FOR DETERMINING v FROM $t_1$, $\Delta t$, AND R*

*FIG. 14*

METHOD AND APPARATUS FOR MEASURING UNDERGROUND FLUID FLOW CHARACTERISTICS

BACKGROUND OF THE INFORMATION

The present invention pertains to methods and apparatus for radioactive well logging. More particularly, the present invention relates to techniques for determining azimuth and speed of horizontal fluid flow in earth formations in the vicinity of a well borehole by the employment of neutron activation of the fluid and the analysis of resultant gamma radiation based on count rate data obtained as functions of horizontal direction and time.

In secondary and tertiary recovery of petroleum deposits, many of the recovery techniques employ the injection of water or chemical solutions into the earth formations comprising the reservoir from injection wells. In planning the recovery operation, the injection of water or chemicals has, in the past, been limited by certain assumptions and/or approximations concerning the mobility of fluid in the formation comprising the reservoir. Crucial factors in such fluid injection programs include the vertical conformity of the producing formation as well as the horizontal permeability and uniformity. In some reservoirs, formation lensing or horizontal partitioning by permeability barriers, such as faults, can occur. In such instances, apparently correlevant intervals of permeability may be separated from one well to another in the field by such formation lensing or permeability barriers being interposed across the interval of formation between the wells.

It is therefore apparent that some knowledge of the existence of such lensing or permeability barriers could prevent the injection of large amounts of costly chemicals or water into a recovery pattern in which formation continuity between injection wells of a field is partially or totally absent. This could prevent the expenditure of large sums of money, time and effort and a fruitless project to recover secondary or tertiary problem deposits.

Information concerning such structure of the earth formation may be obtained by an evaluation of the direction and speed of formation fluid flow by a borehole in the field. Also, by obtaining such speed and direction of flow measurements at a sufficient number of boreholes throughout the field, a mapping of the total flow throughout a petroleum reservoir may be obtained to help in the operational planning of injection of chemicals or water to assist in determining optimum withdrawal rates. Moreover, a knowledge of the lateral water flow characteristics of a particular formation in a producing field can help greatly in understanding of the reservoir dynamics of the particular reservoir being produced.

It is sometimes desirable in a reservoir with multiple producing intervals for a reservoir engineer to be able to delineate those producing zones which provide the most water influx or water drive to the production of petroleum. The mapping of lateral water movement in all zones both above and below the expected water table in the producing formation should supply this information.

Reservoir engineers have been provided with relatively few and often inaccurate well logging instruments to determine the vertical conformance characteristics of the earth formations comprising a reservoir. As a result, they have suffered from inadequate information concerning the properties of the earth formations making up the reservoir. Radioactive tracer studies of the movement of fluids in the vicinity of a well borehole can be misleading in this respect because of the lack of uniform absorption of the tracer element into the flowing stream of formation water. Also, it is time consuming to provide tracer isotopes with sufficient half life to be injected in an injection well, and observe their movement days or even weeks later at a monitoring or producing well in order to obtain some idea of the lateral flow speed or velocity of fluids in the formations comprising the reservoir. In the present invention, relatively little time delay from the beginning of injection is required to observe fluid movement as this is substantially only a function of hydraulic pressure buildup in the formation.

U.S. patent application No. 698,394, filed June 21, 1976, discloses techniques for analyzing gamma ray count data obtained from activated formation fluid to reveal the horizontal flow speed of the fluid. Measurements of count rate intensity, taken as a function of time, are utilized for this purpose. Information concerning the direction of the horizontal formation fluid flow may be obtained as disclosed in U.S. patent application No. 815,964, filed July 15, 1977. A cluster of three gamma ray detectors is used to simultaneously obtain three count rates. The relative intensities of the count rates, compared to the geometry and orientation of the detector cluster, are interpreted to reveal the azimuthal angle of the flow of the formation fluid.

SUMMARY OF THE INVENTION

Apparatus of the present invention includes a sonde, or downhole well logging tool, equipped with a neutron source. A gamma ray detector is longitudinally displaced, and shielded, from the neutron source within the sonde. A generally cylindrical shield is moveable between an extended configuration, in which the shield contains the detector, and a retracted configuration in which the detector is exposed to receive gamma radiation generally from all lateral directions. The shield features a collimator slot running longitudinally along one side. Thus, when the shield is in the extended configuration, the detector may be exposed to radiation from only a selected direction defined by the extent of the slot. A motor is provided for imparting rotational motion to the shield so that the collimator slot may be selectively rotated about the detector. In this way, radiation count data may be obtained from one selected direction at a time. An assembly of gears and a selectively engageable clutch form a linkage to use the motor for moving the shield between the retracted and the extended configurations. Thus, the shield may be selectively retracted to permit count rate data to be obtained from all lateral directions at a time. The rotational orientation of the shield may be determined by the use of a triggering device which provides a sync pulse whenever the shield passes through a particular rotational position. The triggering device may typically be the combination of a light source and photodetector, and an aperture constructed as part of the gear assembly.

Appropriate control electronics may be provided so that the shield may be selectively extended, retracted, rotated, or stopped from the surface. Similarly, data processing circuitry may be provided for analyzing the count rate data as a function of the angle of orientation of the shield. The aforementioned sync pulse may be used to trigger a counter which divides a complete revolution by the shield into N segments. The counts obtained during rotation through any one such segment are isolated and may be displayed as a function of the corresponding segment, or portion of the shield revolution. Thus, count rate data may be displayed as a function of azimuthal angle, or segment number. A gyrocompass, or other appropriate direction-indicating instrumentation, may be provided to indicate a fiducial direction, which then may be related to the position of the shield slot upon the triggering of the sync pulse.

Further to the method of the invention, the sonde is lowered within a borehole until the neutron source is level with a formation whose fluid characteristics are under investigation. The area is irradiated by the neutron source for a given time interval, then the sonde is lowered beyond the depth of the irradiated formation. With the gamma ray detector operational, and the shield in the extended configuration and rotating, the sonde is slowly raised through the irradiated formation. Count rate data is acquired as a function of the rotational position of the shield, and may also be related to the logitudinal position of the sonde within the borehole. The count rate data thus obtained is analyzed and compared with the azimuthal angle of the shield relative to a fiducial direction. The reduced count rate data indicates the azimuthal angle of the horizontal formation fluid flow, with the greatest radiation intensity generally indicating the direction of the fluid flow.

The counting rate of decay of the radioactive isotope produced in the formation fluid may be interpreted in terms of the flow speed of the formation fluid in the vicinity of the borehole. Two or more logging passes may be made through each irradiated zone to obtain tracer isotope and decay data for this purpose. When such count rate data is acquired, the shield is in the retracted configuration, permitting reception of gamma rays by the detector from all lateral directions. Appropriate techniques for reducing and analyzing such data to obtain flow speed values are disclosed in the aforementioned U.S. Patent Applications.

DESCRIPTION OF PREFERRED EMBODIMENTS

Figure 1:
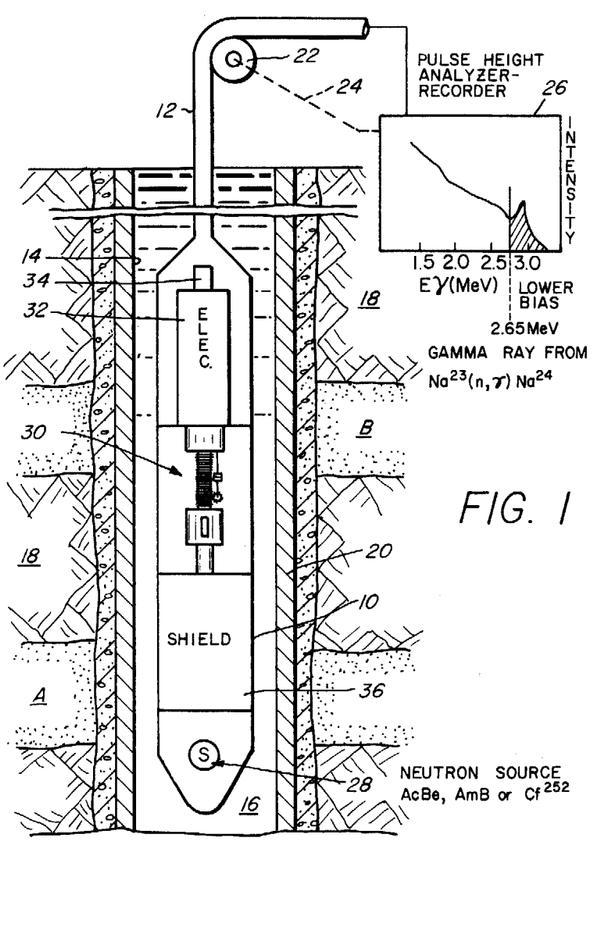
FIG. 1 is an illustration showing schematically a well loging sonde, positioned within a borehole, for horizontal fluid flow detection according to the present invention.
Figure 2:
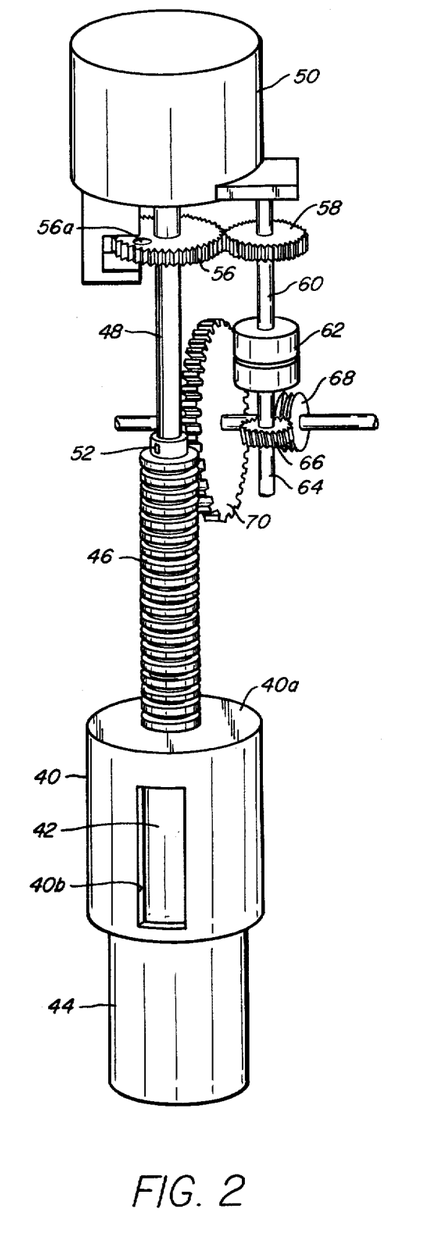
FIG. 2 is a perspective view of the detector and shield assembly of the present invention, with the shield extended over the detector crystal.
Figure 3:
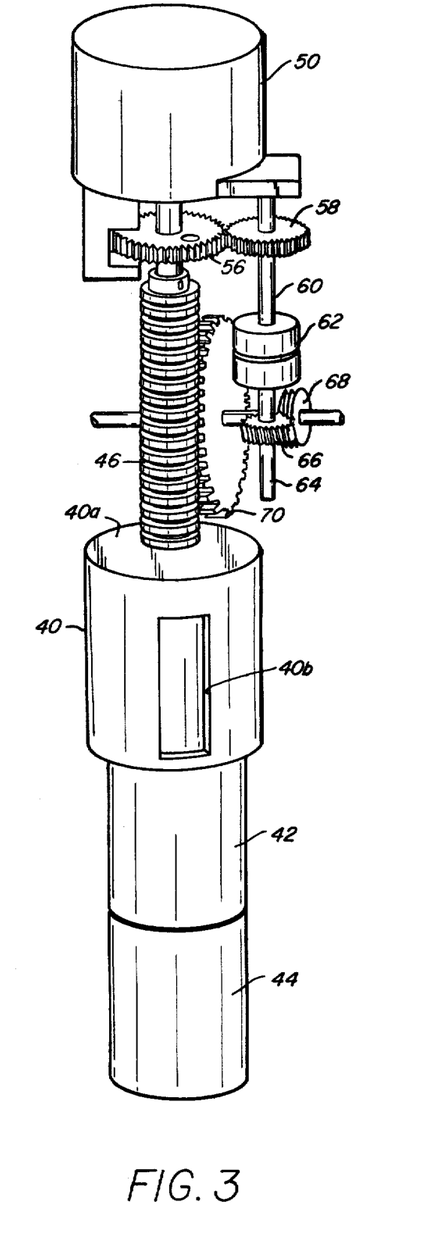
FIG. 3 is a perspective view similar to FIG. 2, with the shield in a retracted position.

Apparatus of the present invention is shown schematically in FIG. 1. A downhole sonde 10 is shown suspended by a well logging cable 12 in a well borehole 14 which is filled with borehole fluid 16 and surrounded by earth formations 18. The well 14 may be lined with casing 20 cemented in place as shown. The cable 12 passes over a sheave 22 which is mechanically or electrically linked, as indicated by the dotted line 24, to a recorder or other display device 26 so that measurements from the downhole sonde 10 may be recorded as a function of depth in the well borehole 14. A neutron source 28 is positioned within the lower end of the sonde 10 for use in radiating formation fluid. The source 28 may be a continuous chemical neutron source such as an actinium berylium source, or a californium 252 source.

Toward the opposite end of the sonde 10 from the source 28 is a detector and shield assembly, indicated generally at 30. A downhole electronic equipment package 32 inlcudes appropriate data handling and control systems, as described in detail hereinafter. Appropriate electrical connections (not shown) are provided between the electronic equipment package 32 and the detector and shield assembly 30. Similarly, the electronic equipment package 32 is appropriately connected to electronic equipment at the surface by way of the cable 12. A gyrocompass, or other appropriate direction-indicating equipment, 34 is provided within the sonde 10 to indicate the direction of orientation of the sonde within the borehole.

Space between the neutron source 28 and the detector and shield assembly 30 in the downhole sonde 10 is occupied by shielding material 36 suitable to prevent direction radiation of the detector with high energy neutrons from the neutron source. Shielding materials with high hydrogen content, such as paraffin or other polymolecular hydrocarbon structure, may be utilized for this purpose. The high hydrogen content serves to slow down or rapidly attenuate the neutron population from the neutron source, and prevent this thermalized neutron population from reaching the vicinity of the detector. To this end, strong thermal neutron absorbers such as boron may be interposed in layers with the hydrogenate shielding material in order to make up the shield portion 36.

The present invention employs the downhole production of radioactive isotopes within the formation fluids in the vicinity of the well borehole 14. For example, the radiation of water in the vicinity of the borehole with high energy neutrons having energy in excess of approximately 10 MEV can result in the creation of the radioactive isotope nitrogen 16 by the nuclear reaction $O^{16}(n,p)N^{16}$. If the formation fluid is saline in nature, the radioactive isotope sodium 24 can be produced by radiating the earth formation with neutrons which are slowed to thermal energy and captured by the isotope sodium 23 comprising NaCl in solution according to the nuclear reaction $Na^{23}(n,\gamma)Na^{24}$. The sodium 24 isotope then decays by the emission of gamma radiation of 2.75 MEV energy. Thus, the detector in the assembly 30 detects the presence of such gamma emission.

Where the neutron bombardment occurs in limestone formations, calcium 49 is also formed, and emits 3.09 MEV gamma rays. However, since the half life of calcium 49 is approximately 9 minutes, the effect of this isotope may be avoided if radiation measurements are delayed even a short time from the end of the radiation time interval. All other significant quantities of naturally occurring gamma rays from radioactive isotopes which may be produced in earth formations using the chemical type neutron source 28 have characteristic energies below 2.65 MEV. Thus, by use of a 2.65 MEV threshold, the radiation detected and counted may be limited, for practical purposes, to that generated by the decay of the unstable radioactive isotope sodium 24.

As described in detail hereinafter, data acquired by use of the detector of the assembly 30 may be analyzed, for example, by the surface electronic equipment, and all information corresponding to gamma rays of less than 2.65 MEV energy may be rejected. A pulse height analyzer, for example, may be used to distinguish only data counts corresponding to gamma rays within selected energy ranges. The selected data counts may be further processed as desired.

Details of the detector and shield assembly 30 are shown in FIGS. 2–5. A collimated shield 40 is made to selectively enclose a cylindrically shaped detector 42. The detector 42 may, for example, be a sodium iodide, thallium-activated scintillation crystal. The crystal 42 is optically coupled to a photomultiplier tube 44 to form a detector assembly. As is well known, gamma rays entering such a crystal 42 interact therewith to produce light flashes, or scintillations, whose intensity is functionally related to the gamma ray energy. The light flashes are then detected by the photomultiplier tube 44 to generate voltage pulses proportional in magnitude, or height, to the intensity of the corresponding light flashes. Thus, a succession of pulses is produced by the detector assembly, wherein each pulse height is proportional to the energy of the corresponding incident gamma ray. The pulse stream from the photomultiplier tube 44 is received by the electronic equipment package 32 for processing before the information relayed therewith is forwarded, along a conductor within the logging cable 12, to the well surface.

It will be appreciated that appropriate power sources (not shown) may be provided at the surface and connected to the downhole electronic equipment package 32 by appropriate conductors within the cable 12 in order to supply operational power for the electronic package as well as the detector and shield assembly 30. As an alternative, power supplies may be included within the electronic package 32. Details of such power supply arrangements and appropriate couplings are not illustrated, as these are conventional in the art.

The shield 40 is generally tubular in shape, with a top plate 40a. A cylindrical rack 46 extends upwardly from the top plate 40a. A collimator slot, or window, 40b extends longitudinally along the side of the shield 40. The slotted shield 40 is thus a collimating device. The dimensions of the slot 40b may vary, but typically the slot may be approximately ½ the length of the shield 40 and may extend through, say, a 60° arc. The cylindrical rack 46 is fixed to the shield 40 so that the motion of the rack is followed by the shield. The rack 46 is hollow, and receives a spline shaft 48 from a motor 50. While the motor 50 may be of any type, a reversible d-c motor will be described. The spline shaft 48 may be the drive shaft of the motor 50, or an extension thereof. The shaft 48 passes within the cylindrical rack 46 and mates with two keys 52 and 54. An enlarged cylindrical end 48a of the shaft 48 rides within the cylindrical rack 46, while the keys 52 and 54 engage matching splines in the shaft to cause the rack and, therefore, the shield 40, to rotate with the shaft regardless of the longitudinal position of the shield relative to the motor 50.

Figures 4, 5:
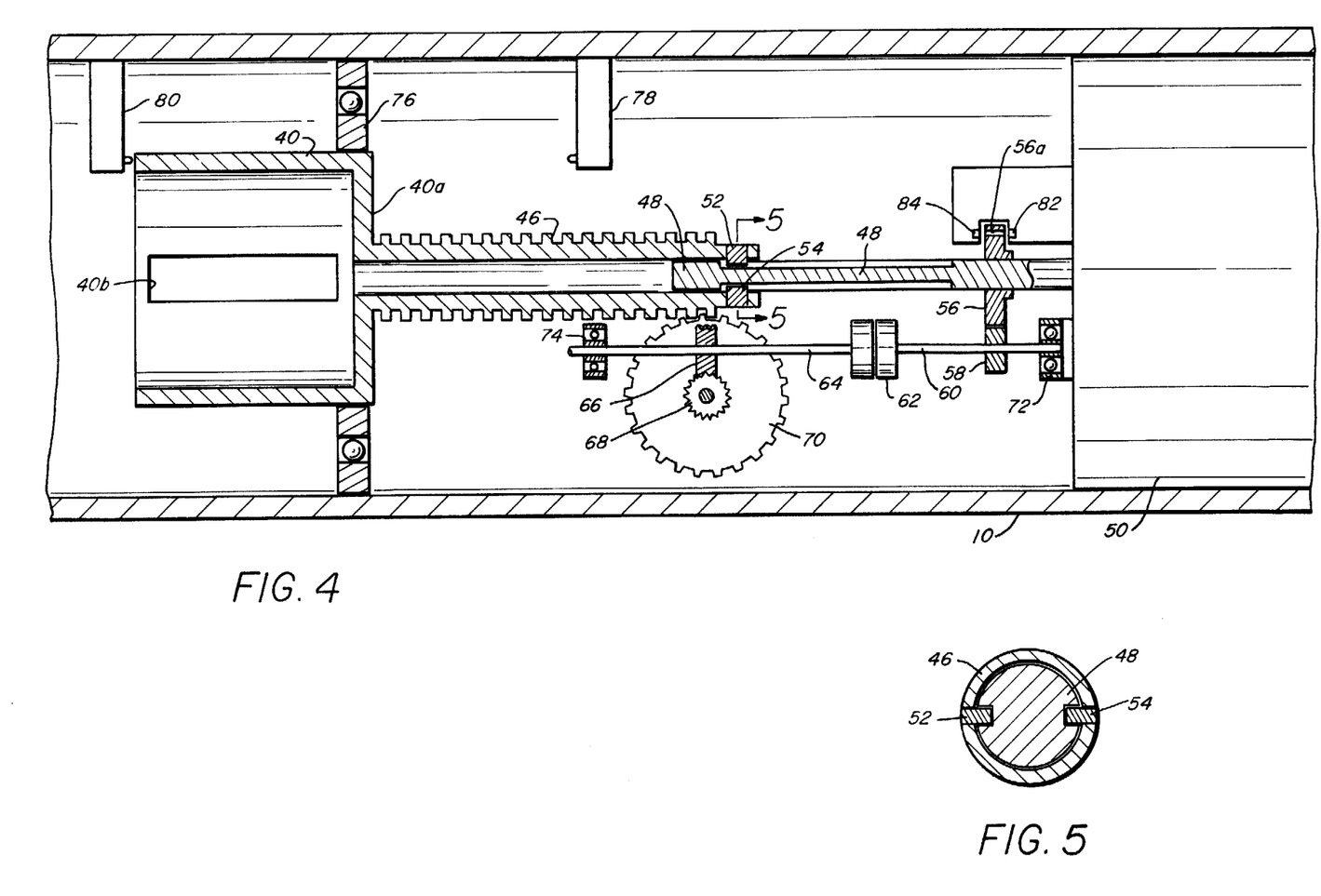
FIG. 4 is a plan view of the shield assembly in partial cross section.
FIG. 5 is a horizontal cross section taken along the line 5—5 in FIG. 4.

A helical gear 56 rotates with the spline shaft 48 adjacent the motor end thereof, causing a spur gear 58 to rotate a linkage shaft 60. The linkage shaft 60 is selectively engaged, by an in-line electromgnetic clutch 62, to a second linkage shaft 64 on which is mounted a helical gear 66. When the clutch 62 is operated to transfer torque from the first linkage shaft 60 to the second linkage shaft 64, the helical gear 66 rotates another helical gear 68 to which is fixed a large spur gear 70. The spur gear 70 meshes with the cylindrical rack 46 to effect longitudinal motion of the cyindrical rack and, therefore, the shield 40. Thus, while the meshing of the spline shaft 48 with the keys 52 and 54 transmits rotational motion from the motor 50 to the cylindrical rack 46 and shield 40, the elements 56 through 70 may be operated to translate rotational motion of the motor 50 into longitudinal motion of the shield 40.

the shafts 60 and 64 are appropriately mounted in bearings, such as 72 and 74. Similarly, the shield 40 moves within an appropriate bearing, such as indicated by 76. Additional bearings and other mounting means may be provided where necessary, particularly to meet the requirements of the construction of the sonde 10. Upper and lower contact switches 78 and 80, respectively, are provided to signal the position of the shield 40 to the control circuitry, as discussed hereinafter.

The helical gear 56 is equipped with a through-bore, or aperture, 56a which may be aligned with a light source 82 and photodetector 84, the later two elements located on opposite sides of the gear 56. Thus, whenever the through-bore 56a is so aligned with the light source 82, light reaches the photodetector 84, which generates a signal, to convey this information, in the form of a voltage pulse to the electronic equipment package 32.

Figure 6:
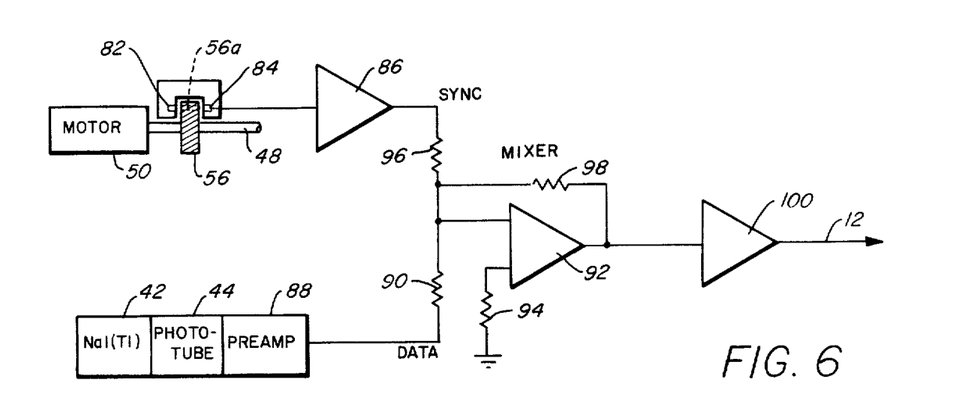
FIG. 6 is a schematic diagram of the data gathering electronic circuitry in the sonde.

The information processing electronic circuitry provided in the electronic package 32 is shown schematically in FIG. 6. The voltage pulse from the photodetector 84 is enhanced by an amplifier 86 to provide a sync pulse to relate the data acquisition by the gamma ray detector to the orientation of the shield 40. The sync signal is combined with the data pulses in a mixer. The voltage pulses generated by the photomultiplier tube 44 are treated by a preamp 88, then supplied by a coupling resistor 90 to the positive input of a differential amplifier 92. The amplifer 92 is referenced to ground by a resistor 94. The output of the amplifier 86 is also supplied by a coupling resistor 96 to the positive input of the amplifer 92. A positive feedback loop, via resistor 98, couples the output of the differential amplifier 92 with its positive input terminal. The sync pulses entering the amplifier 92 are negative, while the data output from the photomultiplier tube 44 is in the form of positive voltage pulses. The effect of the operational amplifier 92 is to invert both the sync and the data pulses, and to mix the two. The mixed data and sync pulses are futher amplified by an amplifier 100, which feeds the signals to a conductor of the logging cable 12.

Figure 7:
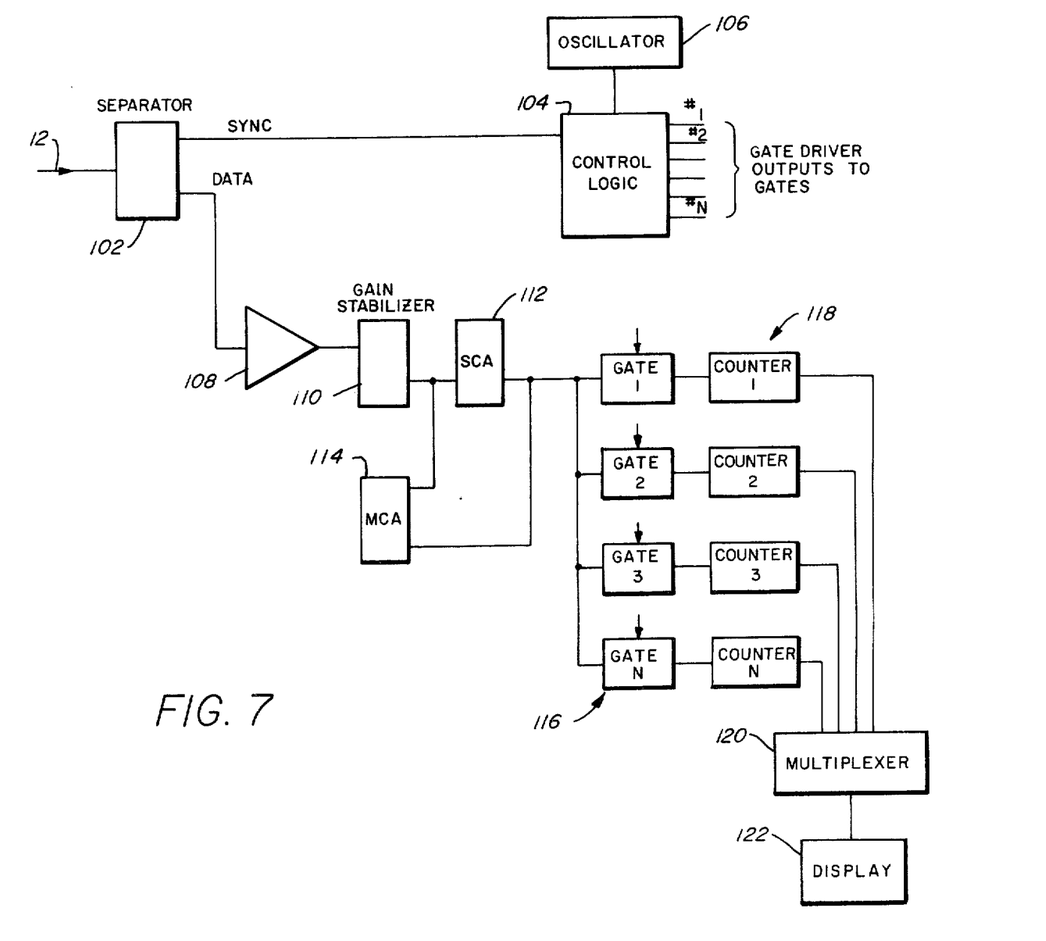
FIG. 7 is a schematic diagram of the data processing electronic circuitry located at the surface.

The data processing electronic equipment, located at the surface, is indicated in FIG. 7. The cable 12 delivers the combined sync and data pulses to a pulse separator 102. The positive sync pulses are isolated and sent to a control logic unit 104, which is driven by an oscillator 106. The control logic unit 104 contains N counters for providing an equal number of gate driver, or trigger, output signals. Thus, the sync pulses are used to synchronize the generation of the gate driver output signals with the rotation of the collimated shield 40. The control logic divides the rotation of the shield 40 about 360° into N segments. For example, where N=12, each segment represents the sweeping of the leading edge of the shield slot 40b through a 30° arc. Each counter is thus triggered to provide a gate driver signal for one of the N segments.

The data pulses from the separator 102 are sent through an amplifier 108 and a gain stabilizer 110 to a single channel analyzer 112 and a multi-channel analyzer 114. The single channel analyzer 112 operates to select the counts of interest based upon their voltage values as reflecting the energies of the corresponding gamma rays detected. Thus, the single channel analyzer 112 may be used to block out, for example, all counts representing gamma rays of energy less than 2.65 MEV. The multi-channel analyzer 114 is used to calibrate the single channel analyzer 112, and to monitor the pulse data acquired by the gamma ray detector.

The counts which are selected are sent to N gates which are controlled by the gate driver output signals from the control logic unit 104. Thus, count data acquired when the collimated shield 40 was in the position corresponding to, for example, the N=2 segment of the arc of rotation are passed by gate number 2 in response to that gate being enabled by the appropriate gate driver output signal when the corresponding data counts are presented. The data signals thus passed by the individual gates are sent to corresponding N counters 118 whose outputs are combined by a multiplexer 120. The multiplexed count information is then presented to a display device 122, such as an osciloscope or printout machine.

Figure 8:
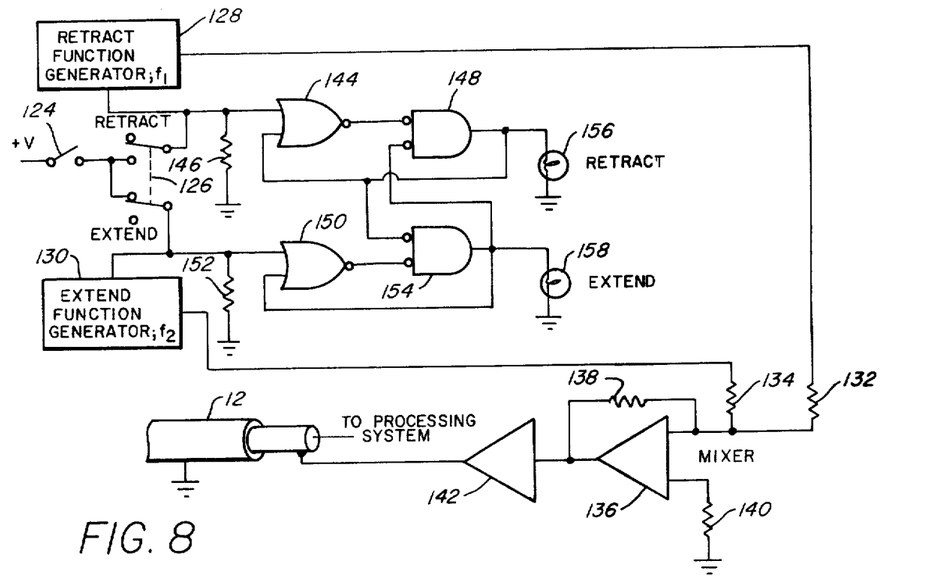
FIG. 8 is a schematic diagram of the control electronic circuitry located at the surface.

Control electronic circuitry located at the surface is shown in FIG. 8. A power switch 124 may be closed to connect a power source to a double pole double throw selector switch 126. The selector switch 126 may be positioned either in a retract mode or an extend mode, as indicated. In the former, the shield 40 is raised in the sonde 10 away from the detector crystal 42. In the extend mode, the shield 40 is lowered over the crystal 42, and permits entry of gamma rays to the crystal only through the collimator slot 40b.

Depending on the position of the selector switch 126, a d-c voltage level +V is sent to one or another of two function generators 128 or 130. Upon reception of the d-c voltage level, either of the generators 128 or 130 will produce a square wave of unique frequency which is then sent through a coupling resistor 132 or 134 to a mixer including an operational amplifier 136 and a negative feedback loop resistor 138. The amplifier 136 is referenced to ground through a resistor 140. Thus, only upon receipt of the voltage level +V by one or the other of the generators will one of two unique frequencies, $f_1$ or $f_2$, corresponding to the generators 128 and 130, respectively, be received by the operational amplifier to indicate a command to retract or extend, respectively, the shield 40. The signal from the operational amplifier 136 is amplified by an amplifier 142, then impressed on a conductor of the logging cable 12 for transmission to the sonde 10.

When the positive voltage level is supplied to the retract function generator 128, that voltage is also supplied to a NOR gate 144, as well as to ground through a resistor 146. The output from the NOR gate 144 is supplied to one of the inputs of an inversion-input AND gate 148. Similarly, a positive voltage level suppled to the extend function generator 130 will also appear at an input of a NOR gate 150, as well as be fed to ground through a resistor 152. The output from the NOR gate 150 is presented to an input of an inversion-input AND gate 154. The output from the first AND gate 148 is supplied to a retract indicator 156, as well as to the other input of the AND gate 154 and the other input of the NOR gate 144. Similarly, the output from the AND gate 154 is supplied to an extend indicator 158, as well as the remaining inputs to the AND gate 148 and the NOR gate 150. This logic circuit has the effect of turning on the appropriate indicator 156 or 158 to indicate whether the selector switch has been turned to the retract or extend mode, and maintaining the respective indicator turned on until the selector switch 126 has been reversed. Thus, for example, with the selector switch 126 in the extend mode as shown in FIG. 8, the extend indicator 158 will be turned on, and the retract indicator 156 turned off. This condition will remain until the selector switch is moved to the retract mode with the power switch 124 closed. Then the condition indicators 156 and 158 will be reversed. These indicators 156 and 158 may be lights, or other devices which operate on the application of a voltage thereto.

Figure 9:
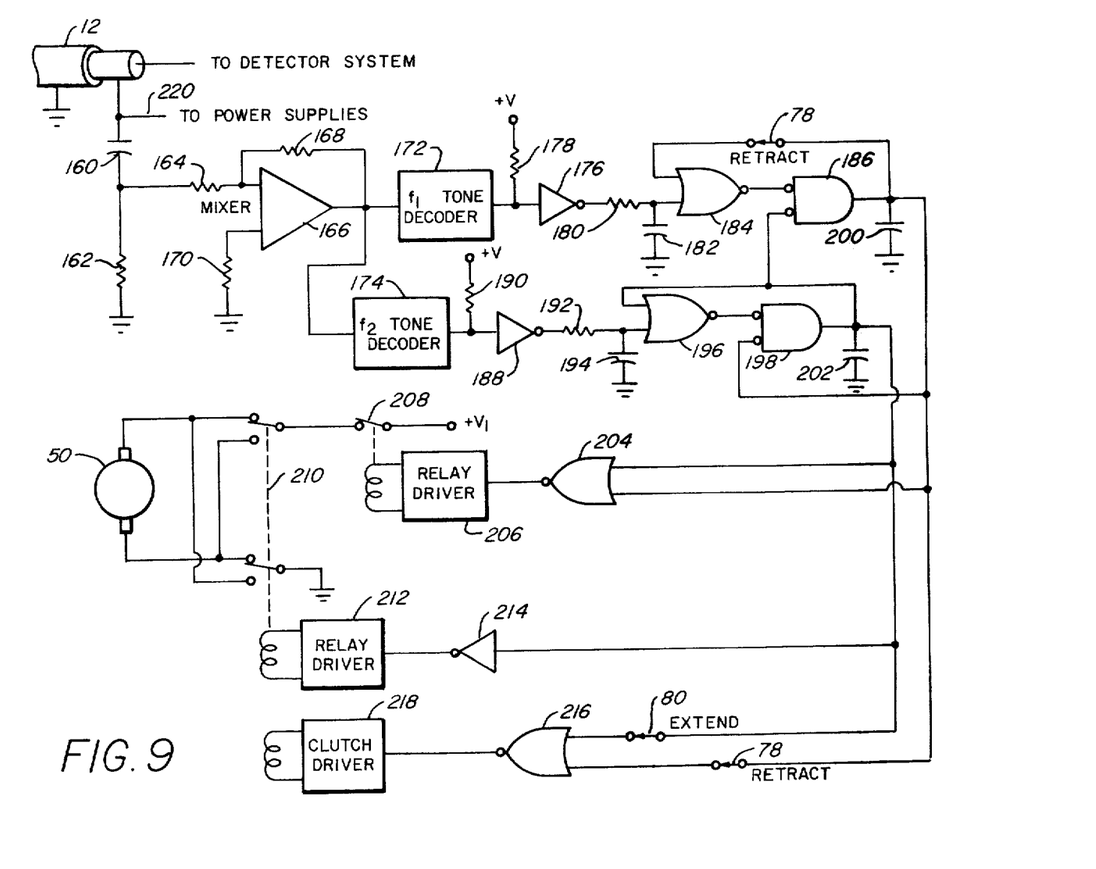
FIG. 9 is a schematic diagram of the control electronic circuitry in the sonde.

Control electronic circuitry located in the electronic equipment package 32 within the sonde 10 is illustrated in FIG. 9. The signal transmitted by the logging cable 12 from the amplifier 142 (FIG. 8) is differentiated by the combination of a capacitor 160 and resistor 162. The resulting sequence of positive and negative voltage spikes is sent, through a coupling resistor 164, to a mixer including an operational amplifier 166 and a feedback loop resistor 168. The operational amplifier 166 is referenced to ground through a resistor 170.

The output from the operational amplifier 166 is supplied to two phase locked loop tone decoders 172 and 174. The tone decoder 172 responds to an input signal of the frequency $f_1$ of the signal generated by the retract function generator 128 to generate a square wave output signal of the same frequency. Similarly, the tone decoder 174 generates a square wave output signal in response to reception of an input signal of frequency $f_2$, the frequency of the signal generated by the extend function generator 130. In that case, the frequency of the signal generated by the tone decoder 174 is also $f_2$. Since the selector switch 126 determines which of the signals of frequency $f_1$ or $f_2$ from the function generators 128 and 130, respectively, will be transmitted along the cable 12 to the sonde control electronics, the signal output from the amplifier 166 will be of either frequency $f_1$ or $f_2$. Consequently, only one of the tone decoders 172 and 174 will generate a characteristic output signal at a time.

When an output signal is generated by the tone decoder 172, this square wave of frequency $f_1$ is supplied to an inverting amplifier 176, which is biased to $+V$ volts through a resistor 178. The output from the amplifier 176 is converted to a d-c voltage level by an integrator including a resistor 180 and a capacitor 182. The resulting d-c voltage level is supplied to a NOR gate 184, whose output is supplied to an inversion-input AND gate 186.

Similarly, when an output signal is generated by the tone decoder 174 at frequency $f_2$, this signal is supplied to an inverting amplifier 188 which is biased to $+V$ volts through a resistor 190. The output from the amplifier 188 is converted to a d-c voltage level by an integrator including a resistor 192 and a capacitor 194. The resulting d-c voltage level is supplied to a NOR gate 196, whose output is supplied to an input of an inversion-input AND gate 198.

The output from the AND gate 186 is supplied to the other input of the AND gate 198, and the output from the AND gate 198 is likewise supplied to the remaining input of the AND gate 186. The AND gate 198 output is also supplied to the remaining input of the NOR gate 196. Similarly, the output from the AND gate 186 is supplied through the retract micro switch 78 of FIG. 4 to the remaining input of the NOR gate 184. Thus, the feedback loop from the AND gate 186 to the NOR gate 184 is closed only when the retract micro switch 78 is closed.

The outputs from the AND gates 186 and 198 are supplied to the two inputs of a NOR gate 204, and are also filtered through grounded capacitors 200 and 202, respectively. The output from the NOR gate 204 is supplied to a relay driver 206 which operates to close a normally open power relay 208. Closing the power relay 208 provides power to operate the motor 50, here, from a 28 volt d-c power source (not shown). Thus, the motor 50 is operated in response to the closing of the power switch 124 with the selector switch 126 in either position.

A selector relay 210 of the double pole double throw type is normally in the position illustrated in FIG. 9 to operate the motor 50, when the power relay 208 is closed, so as to retract the shield 40 when the clutch 62 is engaged. This selector relay 210 is operable by a relay driver 212 to move to a configuration wherein the shield 40 may be extended over the detector crystal 42. The output from the AND gate 198 is supplied to an inverting amplifier 214, whose output signal operates the relay driver 212. Thus, the motor 50 is caused to rotate so as to extend the shield 40 over the crystal 42 only in response to the reception at the amplifier 214 of an output signal from the AND gate 198. This signal is forthcoming only when the tone decoder 174 receives a signal of frequency $f_2$, which, in turn, occurs only with the selector switch 126 in the extend configuration.

The output from the AND gate 198 is also supplied to the extend micro switch 80 of FIG. 4 and, with this switch closed, to a NOR gate 216. Output from the AND gate 186 is similarly supplied through the closed retract micro switch 78, to the other input of the NOR gate 216. Thus, with either tone decoder 172 or 174 receiving the appropriate corresponding input signal, and with the corresponding switch 78 or 80 closed, the NOR gate 216 is enabled to generate an output signal which is supplied to a clutch driver 218. The clutch driver 218, when so operated, causes the engagement of the electromagnetic clutch 62 of FIG. 4.

The micro switches 78 and 80 are normally closed, and are open only when contacted by the shield 40. Thus, the shield 40 is illustrated in FIG. 4 as holding open the micro switch 80 shown schematically therein. Under these conditions, the retract micro switch 78 is closed. It is, therefore, possible to enable the NOR gate 216 to cause the clutch driver 218 to engage the electromagnetic clutch 262 only by use of an output signal from the appropriate AND gate 186 or 198, depending on which of the switches 78 or 80 is closed. Thus, with the shield 40 in the configuration illustrated in FIG. 4, positioning the selector switch 126 in the extend configuration to ultimately cause an output signal from the AND gate 198, with the extend micro switch 80 open, will not cause the clutch 62 to be engaged. In that instance, only by placing the selector switch 126 in the retract configuration may an enabling signal be caused to reach the NOR gate 16, through the closed retract micro switch 78 to cause the clutch 62 to be engaged. In such case, then, the selector relay 210 is in the configuration illustrated in FIG. 9. With the output signal from the AND gate 186 enabling the NOR gate 204 to cause the relay driver 206 to close the power relay 208, the motor 50 rotates, with the clutch 62 engaged to cause the spur gear 70 to rotate to move the rack 46, and, therefore, the shield 40, upwardly along the sonde 10 to the retract position in which the detector crystal 42 is exposed in all lateral directions.

Once the shield 40 has engaged the retract micro switch 78, this switch is open, and the signal from the AND gate 186 no longer reaches the NOR gate 216. Therefore, the clutch 62 is disengaged, and the helical spur gear 70 ceases rotation. At this point, as well as while the shield 40 is being retracted, the extend micro switch 80 is closed. However, with the selector switch 126 in the retract configuration, no signal is generated by the tone decoder 174, and, therefore, no output signal is generated by the AND gate 198 to reach the NOR gate 216.

With the extend micro switch 80 closed, the shield 40 may be extended by moving the selector switch 126 into the extend configuration to cause the tone decoder 164 to generate a signal, thereby producing an output signal from the AND gate 198. This signal from the AND gate 198 is then fed by the micro switch 80 to the NOR gate 216, causing the clutch driver 218 to engage the electromagnetic clutch 262. Also, the output from the AND gate 198 ultimately causes the selector relay 210 to be drawn, by the relay driver 212, into the extend configuration, thereby reversing the direction of rotation of the motor 50 upon the closure of the power relay 208. This power relay 208, as noted hereinbefore, is closed by the enabling of the NOR gate 204 by the output from the AND gate 198. Then, the spur gear 70 is caused to rotate in the direction opposite from that required for the retracting operation, and thus causes the shield 40 to be extended down over the detector crystal 42. While this is occurring, the retract micro switch 78 is closed. However, no signal is generated by the tone decoder 172, and, therefore, there is no output signal from the AND gate 186. When the shield 40 engages the extend micro switch 80, and opens the switch as in the configuration illustrated in FIG. 4, the NOR gate 216 is no longer enabled, and the clutch 62 is disengaged. When this occurs, as noted hereinbefore, the spur gear 70 is no longer rotated to impart longitudinal motion to the rack 46 and the shield 40.

The combination of gates 182, 186 and 196, 198 function similarly to the combination of gates 144, 148 and 150, 154 of FIG. 8. Thus, the crossover of outputs to inputs between the AND gates 186 and 198 guarantees that only one or the other of these gates will be enabled at a time. Also, the feedback loop from the output of either of the AND gates 186 or 198 to the corresponding NOR gate 184 or 196 maintains the output of the corresponding AND gate constant, even after the signal from the corresponding tone decoder 172 or 174 has ceased. Thus, at the end of the extend operation wherein the shield 40 has opened the extend micro switch 80, the output from the AND gate 198 will remain constant to cause the relay driver 212 to hold the selector relay 210 in the extend configuration, and to enable the NOR gate 204 to maintain the relay driver 206 holding the power relay 208 closed. This condition continues until either the power switch 124 is opened or the selector switch 126 is moved into the retract configuration. However, at the end of the retract operation when the shield 40 has opened the retract micro switch 78, the feedback loop from the output of the AND gate 186 to the input of the NOR gate 184 is opened. Then, should the tone decoder 172 cease to provide a signal to the input of the NOR gate 184, the AND gate 186 will cease to provide an output signal to enable the NOR gate 204, resulting in the opening of the power relay 208.

In the particular electronic circuitry illustrated in FIGS. 8 and 9, an appropriate power supply, or supplies, may be located within the electronic equipment package 32 in the sonde 10 to provide the necessary power to operate the downhole control electronic circuitry of FIG. 9. Where necessary, such power sources may be triggered to operate upon the reception of a signal from the surface amplifier 142, with the trigger signal simply tapped from the cable 12 as indicated at 220 in FIG. 9. Thus, whenever a signal, generated either by the retract function generator 128 or the extend function generator 130, is transmitted along the cable 12 to the point 220, the downhole control electronics of FIG. 9 is not only selectively operated by such signal, but has its downhole power sources rendered operable. A similar power triggering system may be employed for the downhole information processing circuitry shown in FIG. 6.

It will be appreciated that, whenever the power switch 124 is closed, and a signal generated by either of the function generators 128 or 130 is transmitted to the sonde 10, an enabling signal is presented to the NOR gate 204 to operate the relay driver 206 to close the power switch 208. As a result, the motor 50 is made to turn in one direction or another depending upon whether the relay driver 212 has received a signal from the AND gate 198. Then, the engagement of the keys 52 and 54 with the spline shaft 48 (FIGS. 4 and 5) causes the rack 46 and the attached shield 40 to rotate. This occurs regardless of whether the NOR gate 216 receives an enabling signal to cause the clutch driver 218 to engage the electromagnetic clutch 62. Consequently, anytime the motor 50 is made to rotate, so too will the shield 40. However, the spur gear 70 is driven to propel the rack 46 and shield 40 longitudinally only when an enabling signal is received, by way of the appropriate closed micro switch 78 or 80, at the NOR gate 216. Therefore, by operation of the two switches 124 and 126 at the surface, the shield 40 may be either retracted or extended, and may be made to rotate, for example, in the fully extended position. Opening the power switch 124 simply causes the shield 40 to remain motionless relative to the sonde 10 at its current location.

Consider an underground formation containing saline water, such as A or B in FIG. 1. The formation, such as A, may be irradiated by generating neutrons with the neutron source 28 while the sonde 10 is positioned with the neutron source at the level of the formation. During this time, the data processing electronic equipment associated with the detector, as well as the photomultiplier tube 44, may be turned off. After the formation A has been sufficiently radiated, the sonde may be lowered below the level of the formation, and slowly raised through the formation with the detector and data processing electronic equipment operating. As an alternative, the sonde may be held stationary with the detector crystal 42 at the level of the formation A.

With the shield 40 in the fully extended position, and the photomultiplier tube 44 and data processing electronic equipment operable, gamma rays resulting from the decay of the sodium 24 isotope produced in the formation fluid may be counted by way of their interactions with the crystal detector 42. The resulting voltage pulses generated by the photomultiplier tube 44 are processed, as described hereinbefore, to produce a printout, or readout, display by the display device 122 shown in FIG. 7. The data thus acquired represents radiation detected only from the direction of orientation of the slot 40b. If the shield 40 is made to rotate by the generation of a signal by the extend function generator 130, as described hereinbefore, the direction from which gamma rays may be detected rotates with the shield 40. The result is that, as the shield 40 is made to rotate, counts are obtained from gamma rays coming from specific directions relative to the sonde 10 at the level of the formation A, with the direction continually changing. These counts may then be displayed by the display device 122 as a function of the instantaneous angle of orientation of the collimator slot 40b. In the alternative, the presentation of the count data may be made relative to the particular N gates through which the counts are processed in the data processing equipment of FIG. 7, again, generally as a function of the angle of orientation of the collimator slot 40b.

Figure 10:
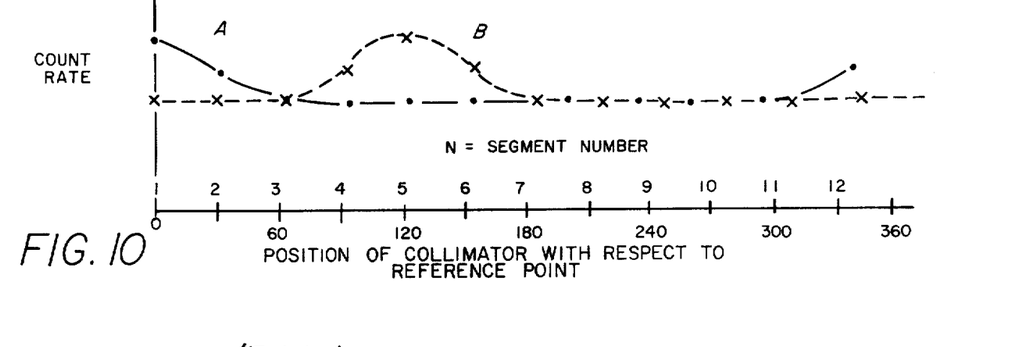
FIG. 10 is a graphical representation illustrating two plots of measured counting rates taken from the display unit as functions of azimuthal angle as well as segment number.

FIG. 10 illustrates how such count data may be presented as a function both of the angle of orientation, in a horizontal plane, of the collimator slot 40b as well as a function of the N segments. Here, N is set at 12. The cloud of sodium 24 nuclei generated as a result of the radiation by the neutron source 28 would be relatively unchanging in density during the gamma ray detection phase if the fluid in the formation A were not flowing. In that case, the count rates for specific gamma ray energies may be expected to be uniform regardless of the angle of orientation of the collimator slot 40b. The resulting count rate display would be a straight line as a function of angle of orientation of the collimator slot 40b, or, in the alternative, the segment number. However, if the formation fluid is in lateral motion, the isotope cloud drifts with the fluid flow, moving the center of the gamma ray sources away from the position of the sonde 10 and, therefore, the detector crystal 42. In such case, the array of gamma ray-producing sodium 24 nuclei is assymetrically situated relative to the crystal detector 42. Then, as the shield 40 is caused to rotate, the intensity of gamma rays reaching the crystal detector 42 varies with the angle of orientation of the collimator slot 40b. The result is a curve such as A in the graph of FIG. 10. In this instance, the relative peak in curve A at 0 degrees, or segment number 1, indicates that the fluid flow in the formation A is moving the gamma ray source nuclei generally in the direction identified as the beginning of segment number 1, or zero degrees. Consequently, when the shield 40 is oriented with the collimator slot 40b toward that particular direction, the counts recorded by the data processing equipment, and presented by the display device 122, are highest. As the shield rotates from this particular direction, the count rate falls off to a lower, relatively constant level for most other angles of orientation of the shield 40.

The curve B in FIG. 10 may reflect similar readings obtained in another formation, such as B in FIG. 1. Thus, the formation B may be irradiated with the neutron source 28 at that level, and the sonde later lowered to position the detector crystal 42 in the formation B. As the extended shield 40 is caused to rotate as before, and gamma rays detected at various selected angles determined by the angle of orientation of the collimator slot 40b, count rate data may be acquired and displayed by the device 122 to provide the curve B as shown in FIG. 10. The peak in the curve B indicates that the fluid flow is in the direction identified as 120°, or the beginning of segment number 5. By using the direction finding device 34 of FIG. 1 to define the angles of orientation of the collimator slot, as presented on the chart of FIG. 10, relative the ground, the direction of flow in both formations A and B, relative to the ground, may be determined by the position in the chart of FIG. 10 of the peaks of the relative data processing output curves A and B respectively.

By taking repeated readings of the gamma ray emissions of the isotope sodium 24 in a particular formation, and obtaining the resulting count rate curves as illustrated in FIG. 10, information as to the rate of fluid flow in that formation may also be obtained. Thus, as the cloud of gamma ray producing nuclei continues to move with the flow of formation fluid, the relative height of the peak of the corresponding curve in FIG. 10 increases. Actually, the portion of the curve away from the peak diminishes, leaving the peak more pronounced, although the actual peak intensity also diminishes. The rate at which the peak curve of FIG. 10 changes relative to the times at which such measurements are made is related to the rate of flow of the formation fluid.

Intensity of gamma ray activity may also be used to determine the speed of the horizontal flow of the saline water in an irradiated formation, as described in the aforementioned Patent Applications. To obtain such detailed information, the shield 40 may be retracted to expose the crystal detector 42 on all sides. Then, with the particular formation irradiated by way of the neutron source 28, the sonde may be lowered below the level of the formation, and slowly raised through the formation with the photomultiplier tube 44 and the associated data processing equipment operable. Then, if the formation fluid is not in motion, the observed decrease in activity with time t will follow the exponential decay $e^{-\lambda t}$ wherein $\lambda$ is the decay constant of the induced radioactivity. However, if the fluid is in motion in a horizontal direction relative to the borehole 14, the observed decrease in activity will be due to the exponential decay characteristic plus an additional decrease due to the motion of the radioactive nuclei from the vicinity of the detector crystal 42 by the moving fluid.

Figure 11:
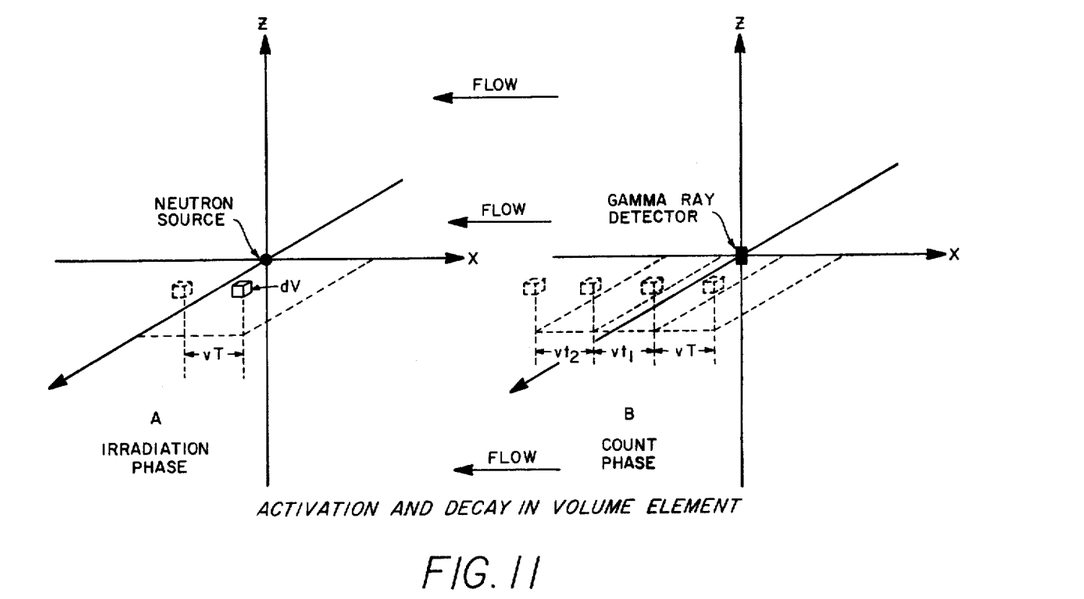
FIG. 11 is a schematic diagram illustrating the geometry of the neutron activation and radioactive decay of a small volume element of formation fluid.

With reference to FIG. 11, consider a point neutron source positioned at the origin $x=y=z=0$ of the coordinate axes of the figure within a flowing fluid having a linear velocity v in the minus x direction of the coordinate system. Then, if this fluid is irradiated with neutrons for a time interval T, the gamma ray activity induced within a small volume element dV whose position is (x,y,z) at the beginning of the neutron radiation is given by the expression of Equation 1.

$$dA(T,v,x,y,z) = \frac{A_o \Sigma dV}{4\pi} \lambda e^{-\lambda T} \int_o^T \psi(t) e^{\lambda t} dt \quad (1)$$

where $A_o$ = neutron source strength in neutrons/sec, $\lambda$ = decay constant of the radioactive isotope of interest, and $\epsilon = N_0 \rho \sigma p_i / 100 \, M_i$ where $N_0$ = Avogadro's number, $\rho$ = the density of the liquid, $\sigma$ = the cross-section for the radiation producing the radioactive isotope of interest, $p_i$ = the percentage abundance of the target isotope within the liquid, and $M_i$ = the atomic weight of the target isotope.

In Equation 1 the term $\psi$ represents the thermal neutron flux distribution for a two neutron group diffusion model, and is given by the expression of Equation 2 as follows:

$$\psi = \frac{((x-vt)^2 + y^2 + z^2)^{\frac{1}{2}}}{S_2(L_1^2 - L_2^2)} \cdot \{e^{-((x-vt)^2+y^2+z^2)^{\frac{1}{2}}/L_1} - e^{-((x-vt)^2+y^2+z^2)^{\frac{1}{2}}/L_2}\} \quad (2)$$

where $S_2$ = the slowing down power, $L_1$ = the diffusion length for the first neutron group (fast neutrons), and $L_2$ = the diffusion length for the second group (thermal neutrons).

If the neutron source is then removed and a gamma ray detector is positioned at $x=y=z=0$ of the coordinate axes as is illustrated in FIG. 11, the induced radioactivity from the volume element dV registered within the detector at some time t measured from the end of the irradiation time interval T is given by the expression of Equation 3:

$$df(T,t,v,x,y,z) = E_\gamma \frac{dA(T,v,x,y,z)e^{-\lambda t}}{4\pi} \cdot \frac{\exp -\mu((x-v(t+T))^2 + y^2 + z^2)^{\frac{1}{2}}}{(x-v(t+T))^2 + y^2 + z^2} \quad (3)$$

where $E_\gamma$ = the efficiency of the detector for the gamma radiation of interest, and $\mu$ = the linear attenuation coefficient for the gamma radiation of interest.

Now substituting Equation 1 into Equation 3 and integrating over all volume elements dV, the total radioactivity registered by a detector at time t is obtained by the expression of Equation 4 as follows:

$$f(T,t,v) = \frac{\lambda A_o E_\gamma \Sigma e^{-\lambda(t+T)}}{(4\pi)^2} \int_x \int_y \int_z \{\int_0^T e^{\lambda\psi} dt\} \cdot \quad (4)$$
$$\frac{\exp - \mu((x - v(t+T))^2 + y^2 + z^2)^{\frac{1}{2}}}{(x - V(T+t))^2 + y^2 + z^2} dxdydz$$

Equation 4 can be integrated numerically in order to evaluate the integral term thereof.

Figure 12:
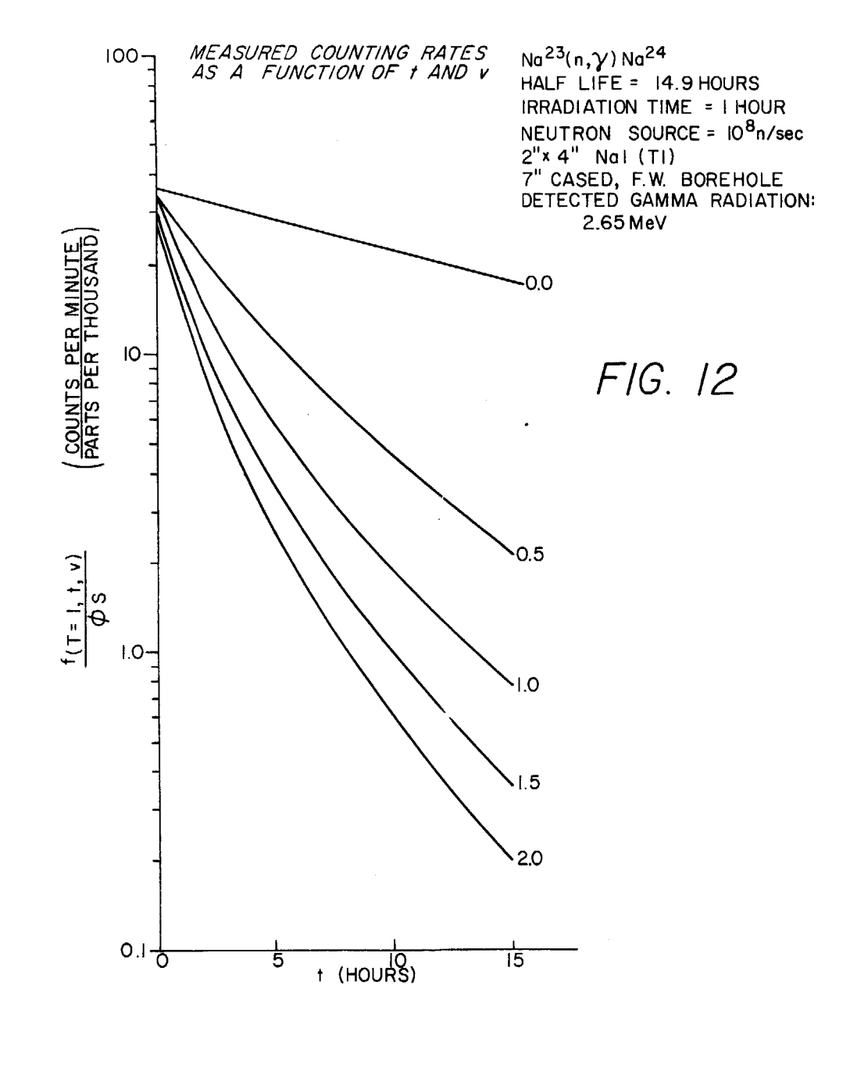
FIG. 12 is a graphical representation illustrating measured counting rates as functions of time and a speed of horizontal fluid movement of fluid in the vicinity of a well borehole.

If it is now assumed (1) that the fluid is contained in a permeable formation of porosity $\phi$, (2) that the reaction of interest is only the $Na^{23}(n,\gamma)Na^{24}$ reaction having a half life of approximately 14.9 hours, and (3) that all of the sodium contained in the formation is contained in the formation fluid in the form of sodium chloride, then the term $\Sigma$ of Equation 4 can be expressed in terms of $\phi$, the porosity and S, the salinity of the formation fluid. FIG. 12 shows the general form of the function $f(T,t,v)/\phi S$ as a function of time t for the 2.75 MEV gamma radiation from the reaction $Na^{23}(n,\gamma)Na^{24}$. In FIG. 12 the constants of Equation 3 are taken to be as follows:

$\lambda = 0.0465$ hours$^{-1}$,
$T = 1.0$ hour,
$A_o = 10^8$ neutrons/second,
$S =$ is the salinity of the formation fluid in parts per thousand (ppt) sodium chloride, and
$\phi =$ the formation porosity (fractional).

The remaining constants in Equation 4 for the function $f(T,t,v)$ are obtained from the normalization of data taken in controlled test formations with known borehole conditions. Data taken in a cased fresh water filled 7 inch borehole and using a 2 inch by 4 inch thallium-activated sodium iodide scintillation counter crystal were used in obtaining the curves of FIG. 12.

In FIG. 12 it can be observed that the decay rate at zero velocity is a straight line on the logarithmic scale of the presentation of the figure. The family of curves below the zero velocity curve show the effect of the linear velocity of the flowing fluid on the decrease in counting rate as a function of time for the values of the constants chosen in this representation.

It will be shown subsequently that a knowledge of S and $\phi$ is not required in order to obtain v the linear flow speed in the horizontal direction. These quantities do, however, affect the recorded counting rates which in turn affect the statistical accuracy of the computed quantity v, the linear flow speed in the horizontal direction. It will be appreciated by those skilled in the art that the graphical illustration of FIG. 12 represents one configuration of assumptions pertaining to the formation porosity and salinity of the formation fluids, but that other similar relationships may be obtained for different values of water salinity, porosity and detector efficiencies and neutron source strength by the same process of the evaluation according to Equation 4 of these different parameters.

By using FIG. 12, estimates of the counting rate of gamma rays from the decay of the radioactive sodium 24 under field conditions may be obtained. For example, in a formation having a porosity of 30% which is saturated with 100 parts per thousand sodium chloride water which is moving horizontally at a linear velocity of ½ inch per hour, a counting rate recorded at $t=2$ hours after the termination of a $T=1$ hour irradiating period can be shown to be approximately 645 counts per minute. This counting rate would be adequate to provide accurate measurement of the linear flow velocity in a horizontal direction with sufficient statistical accuracy to insure usefulness of the measurement.

Consider the two earth formations A and B penetrated by the well borehole 14 as shown in FIG. 1. To determine the speed and direction of fluid flow, if any, in either of these two formations, a logging operation according to the present invention may be initiated by first positioning the neutron source 28 within zone A and irradiating this zone, for example, for approximately 1 hour with neutrons. The irradiation time interval may be varied and can generally be less than 1 hour if the salinity of the formation, or the strength of the neutron source, is adequate. Once zone A has been irradiated for the desired time interval, the logging sonde 10 is raised to position the neutron source 28 adjacent zone B. Zone B is then also irradiated for the specified time interval with neutrons.

Following the irradiation of zone B, the logging sonde 10 is lowered below zone A, and a continuous logging operation is initiated in which the sonde is slowly raised through zone A. During this pass through zone A, the gamma ray detector is operational, the shield 40 is extended and rotating, and count rate curves, such as shown in FIG. 10, may be acquired. As the detector is raised through the formation, the rate and direction of fluid flow may differ. The count rate curves as shown in FIG. 10 will reflect these variations. Where the direction of fluid flow changes, the curve peak will occur at different azimuthal angles. Where the speed of flow varies, the height and sharpness of the peak will change. For example, a higher formation fluid speed will be indicated by a narrower and relatively taller peak on the count rate curve. Where the flow speed is relatively low, so that the distribution of decaying isotope particles has not shifted relative to the borehole to a great extent during the time interval between exposure to the neutrons and the acquisition of count rate data, the peak will be relatively low and broad.

For each zone A and B, the count rate data with the shield extended and rotating is analyzed as discussed hereinbefore. Thus, for a given level within a zone containing fluid under investigation, one or more count rate curves with the count information plotted as a function of azimuthal angle, or segment number, may be obtained and compared to the fiducial direction established by the use of the gyrocompass, or other direction-indicating apparatus. For each level at which such azimuthal angle information is obtained, the count data may be further analyzed to determine the speed of the fluid flow. As noted hereinbefore, a comparison of relative peak heights and shapes will indicate the rate of fluid flow. The sonde may be held at a given level while multiple count rate curves as in FIG. 10 are obtained over an extended period of time. The curve peaks may then be plotted as a function of time, with the slope of this curve indicating the speed of fluid flow. As an alternative, the shield may be retracted from the detector, and flow speed information obtained on the basis of count intensity as discussed hereinbefore. A separate sonde not equipped with the rotating shield may also be employed for this purpose.

Figure 13:
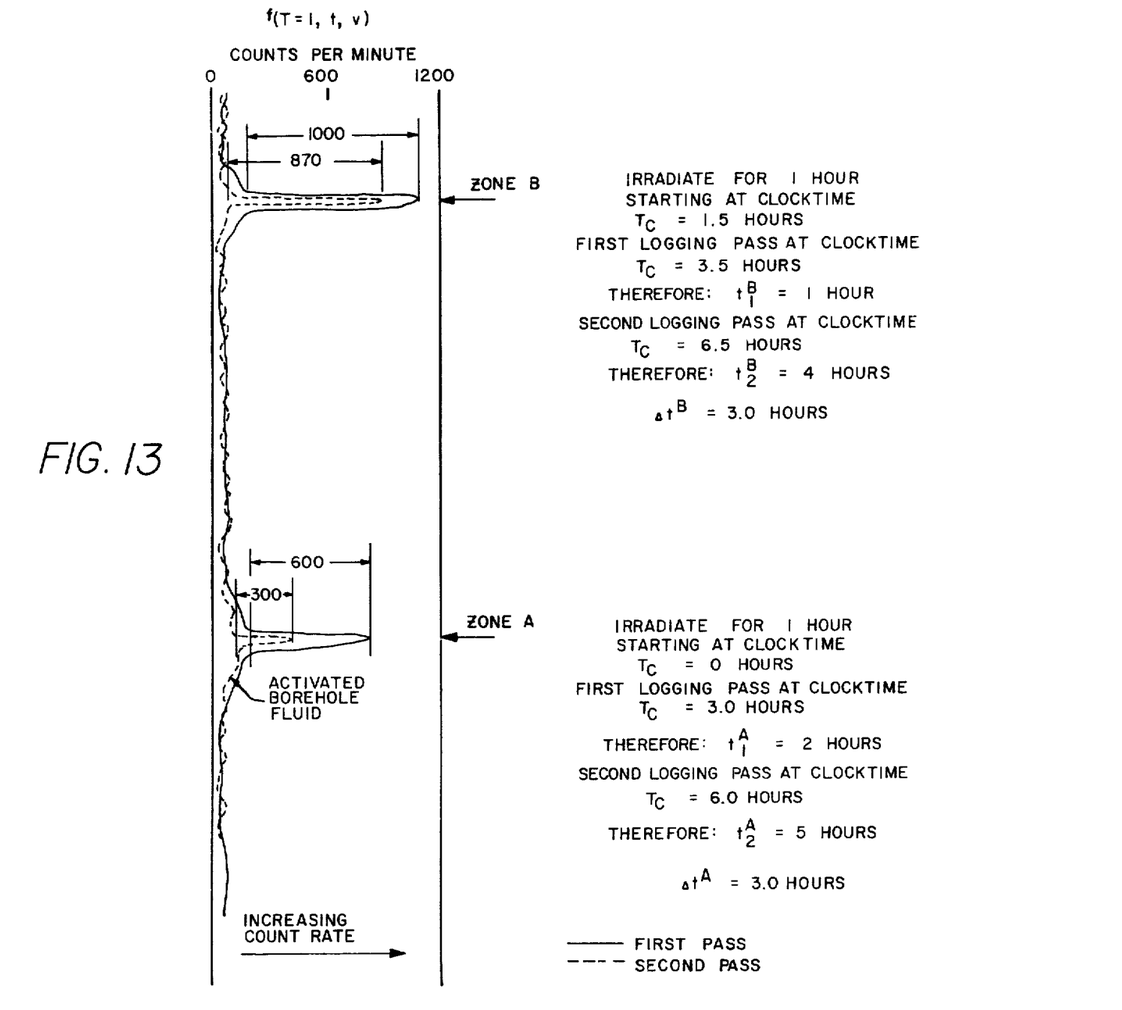
FIG. 13 is a graphical illustration showing a well log according to the present invention.

To evaluate the speed of fluid flow in the two zones A and B based on radiation intensity, multiple logging passes for each zone may be employed. As indicated in FIG. 13, a different count rate curve may be expected for each logging pass through a zone due to a movement of the radiating isotopes between passes. The time $t^4_1$ at which the detector portion of the sonde 10 passes zone A, measured from the end of the irradiation of zone A, is recorded. Similarly, the time $t^B_1$ at which the detector passes the activated region of zone B is measured from the end of the irradiation of zone B and is also recorded. Corresponding times $t^A_2$ and $t^B_2$ are also recorded to mark the second pass of the detector through each zone.

During the neutron activation phase, sodium 24 will also be produced within the borehole fluid 16 if the fluid is saline. However, during the subsequent movement of the sonde 10, this activated borehole fluid 16 will be effectively dispersed up and down the borehole 14 by the movement of the well logging sonde. It has been found in usage that this dispersal of the borehole fluid 16 is adequate to insure a reduction of the background due to sodium 24 produced in the borehole 14 below a harmful level.

The background count level shown in FIG. 13 is representative of this background sodium 24 produced in the activated borehole fluid 16. As may be seen in FIG. 13, such background radiation is not sufficient to cause confusion between the sharp peaks occurring at the irradiated points of zones A and B.

In order to detect the horizontal flow rates it is only necessary to observe the relatively sharp spikes in the depth logs of FIG. 13 and to relate these to the nomograph of FIG. 14, as described hereinafter. From the example log shown in FIG. 13, the irradiation peak on the first logging run through zone A is approximately 600 counts per minute, while the irradiation peak on the second logging run is approximately 300 counts per minute. For zone A also, $t^A_1 = 2$ hours and $\Delta t_A$, the elapsed time between the second logging run and first logging run past zone A, is three hours. Thus, the ratio of counting rates in zone A, $R_A$, is 2.0 for this example.

For zone B, the counting rate on the first logging pass is approximately 1,000 counts per minute, while the counting rate on the second logging pass is approximately 870 counts per minute. For these two logging passes $t^B_1 = 1$ hour and the elapsed time $\Delta t_B$ between logging passes equal three hours. Thus, the ratio of the count rates on the two logging passes through zone B, $R_B$, is 1.15.

Figure 14:
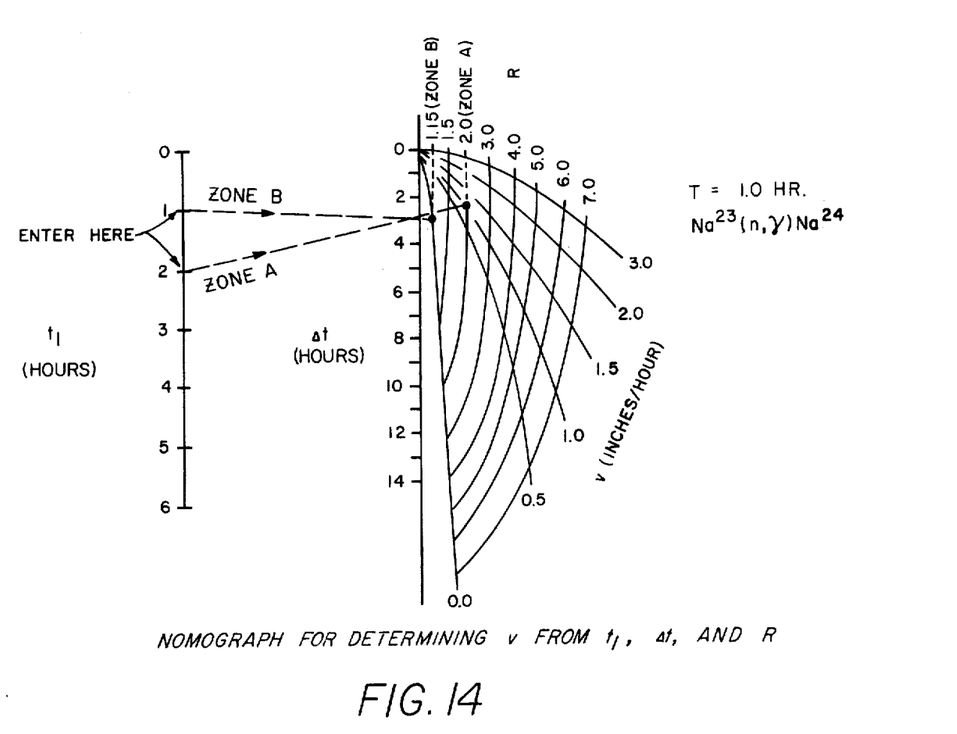
FIG. 14 is a nomograph for interpreting the radiation measurements to determine the speed of fluid flow in the vicinity of a well borehole.

A nomograph constructed from the data plotted in FIG. 12 is illustrated in FIG. 14 in which it is possible to calculate the linear flow rate in the horizontal direction past the irradiated zones. For zone A, a point is obtained on the first line at the left of the nomograph which corresponds to $t^A_1 = 2$ hours. A second point on the second vertical axis to the right is obtained by the value of $\Delta t_A$ which, in this case, equals three hours. A straight line through these two points intersects the curve drawn to the right corresponding to the value of the ratio of counts for the particular measurement (in this case $R_A = 2.0$). The point of intersection indicates that the velocity of horizontal flow which would produce this ratio corresponding to the measurement time intervals is approximately 1.0 inches per hour. Following the same procedure and entering the values of $t^B_1 = 1$ hour and $\Delta t_B = 3$ hours for zone B determines that a ratio of 1.15 is indicative of zero horizontal flow through zone B during the time following the radiation intervals.

The nomograph described with respect to FIG. 14 represents one method of interpretating the measurements performed with the well logging system of FIG. 1. It will be appreciated by those skilled in the art however that this nomograph, or other techniques which are analogous to the solution of the equations involved, may be programmed for use on a general purpose digital computer rather than being interpreted by the hand calculation technique according to the nomograph of FIG. 14. For example, the nomograph of FIG. 14 could be entered in tabular form in the memory of a general purpose digital computer. Appropriate interpolation and extrapolation techniques may be used to obtain the solutions corresponding to the measurement quantity. This type of solution would be apparent to those skilled in the art when presented with the nomograph of FIG. 14 or a nomograph corresponding to the calibration characteristics of a particular sonde.

The sodium 24 tracer which is produced in situ by the neutron irradiation according to the technique of the present invention is an ideal tracer isotope for relatively slow horizontal flow rates because of its long half life of about 14.9 hours and the relatively high energy gamma radiation which it emits upon its decay. If it is desired however to measure water flow rates which are relatively fast (on the order of feed per minute) it could be necessary to use a shorter lived tracer such as nitrogen 16 which has a half life of approximately 7.2 seconds. In such an instance, it would be necessary to utilize a deuterium-tritium accelerator type neutron source rather than a chemical neutron source due to the fact that the $O^{16}(n,p)N^{16}$ reaction has a 10 MEV threshold energy. In this instance, however, the same theory and logging techniques which have been previously discussed with respect to the use of sodium 24 tracer could also be applied using the nitrogen 16 tracer.

The foregoing disclosure and description of the invention is illustrative and explanatory thereof, and various changes in the method steps as well as in the details of the illustrated apparatus may be made within the scope of the appended claims without departing from the spirit of the invention.

We claim:

1. Well logging apparatus comprising:
   (a) a sonde adapted for passage through a well borehole;
   (b) a neutron source with said sonde;
   (c) a gamma ray detector within said sonde longitudinally displaced from said neutron source;
   (d) collimating means for selectively circumscribing said detector to limit detection sensitivity to radiation passing to said detector through said collimating means, and selectively rotatable to vary the rotational orientation of said collimating means relative to said detector; and
   (e) gyrocompass means for identifying the direction of orientation of said collimating means with respect to a fixed reference direction on the surface of the earth.

2. Well logging apparatus as defined in claim 1 further comprising a motor for selectively imparting rotational motion to said collimating means.

3. Well logging apparatus as defined in claim 2 further comprising linkage means for selectively moving said collimating means between an extended configuration, in which said collimating means so circumscribes said detector, and a retracted configuration, in which said detector may be exposed to radiation from all lateral directions.

4. Well logging apparatus as defined in claim 3 wherein said linkage means so moves said collimating means by translating rotational motion of said motor to longitudinal motion of said collimating means.

5. Well logging apparatus as defined in claim 4 wherein said linkage means includes selectively engagable clutch means.

6. Well logging apparatus as defined in claim 5 further comprising control means for selectively operating said motor, and for selectively engaging said clutch means.

7. Well logging apparatus as defined in claim 6 further comprising circuitry for processing gamma ray court information from said detector.

8. Well logging apparatus as defined in claim 7 wherein said detector comprises a scintillation crystal optically coupled to a photomultiplier tube.

9. Well logging apparatus as defined in claim 8 further comprising shielding within said sonde, positioned between said neutron source and said detector.

10. Well logging apparatus as defined in claim 7 wherein said circuitry comprises:
   (a) means for analyzing said gamma ray count information according to the energy of gamma rays counted; and
   (b) means for relating said gamma ray count information, obtained with said collimating means in said extended configuration to the rotational orientation of said collimating means.

11. Well logging apparatus as defined in claim 6 wherein said control means comprises:
   (a) retract signal generation means for selectively generating an oscillatory signal of a first frequency;
   (b) extended signal generation means for selectively generating an oscillatory signal of a second frequency;
   (c) selector means for determining which said oscillatory signal is so generated;
   (d) mixer means for receiving said oscillatory signals so generated;
   (e) retract tone decorder means for generating a retract control signal in response to receiving said oscillatory signal of said first frequency so generated;
   (f) extend tone decoder means for generating an extend control signal in response to receiving said oscillatory signal of said second frequency so generated;
   (g) power control means for operating said motor in response to receiving either said control signal;
   (h) direction control means for selectively determining the rotational direction of operation of said motor; and
   (i) clutch control means for selectively engaging said clutch means.

12. Well logging apparatus as defined in claim 11 wherein said control means further comprises switch means for cooperating with said clutch control means to prevent engagement of said clutch means upon generation of said extend control signal when said collimating means is in said extended configuration, and to prevent engagement of said clutch means upon generation of said retract control signal when said collimating means is in said retracted configuration.

13. Well logging apparatus as defined in claim 1 wherein said detector comprises a scintillation crystal optically coupled to a photomultiplier tube.

14. Well logging apparatus as defined in claim 13 further comprising shielding within said sonde, positioned between said neutron source and said detector.

15. Well logging apparatus as defined in claim 1 further comprising circuitry for processing gamma ray count information from said detector.

16. Well logging apparatus as defined in claim 15 wherein said circuitry comprises:
   (a) means for analyzing said gamma ray count information according to the energy of gamma rays counted; and
   (b) means for relating said gamma ray count information, obtained with said collimating means in said extended configuration, to the rotational orientation of said collimating means.

17. Well logging apparatus as defined in claim 1 further comprising control means for selectively causing said collimating means to so rotate.

18. A method for determining the characteristics of flow of earth formation fluid, moving horizontally past a borehole, comprising the steps of:
   (a) irradiating the formation fluid with neutrons from a neutron source positioned within the borehole;
   (b) providing a gamma ray detector;
   (c) providing a shield at least partially enclosing said detector, said shield being equipped with a slot through which said detector may be exposed to radiation, and said shield being rotatable to vary the angle of orientation of rotation of said slot relative to said detector and providing a means for detecting the direction of the orientation of said shield with respect to a fixed reference direction;
   (d) exposing said detector, through said slot, to radiation from the neutron-irradiated formation fluid to acquire count rate data from said detector as said shield is being so rotated; and
   (e) comparing said count rate data from said detector with the instantaneous angles of orientation of said slot as said data was acquired to determine the direction of movement of said formation fluid.

19. A method as defined in claim 18 further comprising the additional step of analyzing said gamma ray count data according to the energy of gamma rays counted.

20. A method as defined in claim 19 further comprising the additional step of limiting the comparing of said gamma ray count data to that corresponding to gamma rays within a selected energy range.

21. A method as defined in claim 18 further comprising the additional steps of:
   (a) so exposing said detector to radiation from said neutron-irradiated formation fluid a second time to acquire second count rate data;
   (b) so comparing said second count rate data with said direction of orientation of said shield with respect to a fixed reference direction; and
   (c) comparing count rate data from both said exposures to determine flow speed of said formation fluid past said borehole.

22. A method as defined in claim 18 further comprising the additional steps of:
   (a) retracting said shield from said detector;
   (b) exposing said detector to radiation from the neutron-irradiated formation fluid to acquire first additional count rate data;
   (c) waiting a predetermined length of time;
   (d) so exposing said detector to radiation from the neutron-irradiated formation fluid again to acquire second additional count rate data; and
   (e) combining said first and second additional count rate data according to a predetermined relationship to determine flow speed of said formation fluid past said borehole.

23. A method as defined in claim 18 further comprising the additional steps of:

(a) providing means for identifying the direction of orientation of said shield relative to said borehole; and (b) so determining the direction of movement of said formation fluid by identifying said direction of movement relative to said shield and, therefore, relative to said borehole.

* * * * *